US010386179B2

United States Patent
Grenet et al.

(10) Patent No.: US 10,386,179 B2
(45) Date of Patent: Aug. 20, 2019

(54) METHOD OF IDENTIFYING GEOMETRIC PARAMETERS OF AN ARTICULATED STRUCTURE AND OF A SET OF REFERENCE FRAMES OF INTEREST DISPOSED ON SAID STRUCTURE

(71) Applicants: MOVEA, Grenoble (FR); COMMISSARIAT A L'ENERGIE ATOMIQUE ET AUX ENERGIES ALTERNATIVES, Paris (FR)

(72) Inventors: Pierre Grenet, Grenoble (FR); Christelle Godin, Brignoud (FR)

(73) Assignees: Commissariat a L'Energie Atomique Et Aux Energies, Paris (FR); MOVEA, Grenoble (FR)

( * ) Notice: Subject to any disclaimer, the term of this patent is extended or adjusted under 35 U.S.C. 154(b) by 769 days.

(21) Appl. No.: 14/391,645

(22) PCT Filed: Mar. 7, 2013

(86) PCT No.: PCT/EP2013/054563
§ 371 (c)(1),
(2) Date: Oct. 9, 2014

(87) PCT Pub. No.: WO2013/131990
PCT Pub. Date: Sep. 12, 2013

(65) Prior Publication Data
US 2015/0057971 A1 Feb. 26, 2015

(30) Foreign Application Priority Data
Mar. 8, 2012 (FR) ..................... 12 52101

(51) Int. Cl.
*A61B 5/11* (2006.01)
*G01B 21/00* (2006.01)
(Continued)

(52) U.S. Cl.
CPC ............ *G01B 21/00* (2013.01); *A61B 5/1116* (2013.01); *A61B 5/1122* (2013.01);
(Continued)

(58) Field of Classification Search
USPC .................................................. 600/301, 595
See application file for complete search history.

(56) References Cited

U.S. PATENT DOCUMENTS 9,958,470 B2  5/2018  Grenet
2007/0032748 A1  2/2007  McNeil et al.
(Continued)

FOREIGN PATENT DOCUMENTS

EP  1985233 A1  10/2008

OTHER PUBLICATIONS

International Search Report and Written Opinion from PCT/EP2013/054563, dated Apr. 26, 2013.

*Primary Examiner* — Lam S Nguyen
(74) *Attorney, Agent, or Firm* — BakerHostetler

(57) ABSTRACT

Parameters characterizing the orientation and the position of each sensor, including at least one accelerometer, are evaluated in the reference frame of each segment, together with the length of each segment, by using predetermined configurations and motions of a structure to which the sensors are attached. This makes it possible to provide a device for capturing the motions of a body with measurements which enables greater reliability of the measurements.

15 Claims, 8 Drawing Sheets

(51) Int. Cl.
*G06F 3/01* (2006.01)
*G01P 15/00* (2006.01)

(52) U.S. Cl.
CPC ............ *A61B 5/1126* (2013.01); *G01P 15/00* (2013.01); *G06F 3/011* (2013.01); *A61B 2562/0219* (2013.01); *F04C 2270/041* (2013.01)

(56) References Cited

U.S. PATENT DOCUMENTS

| | | | | |
|---|---|---|---|---|
| 2009/0204031 A1* | 8/2009 | McNames | ............ | A61B 5/1071 600/595 |
| 2012/0172681 A1* | 7/2012 | Sun | ........................ | A61B 5/067 600/301 |

* cited by examiner

METHOD OF IDENTIFYING GEOMETRIC PARAMETERS OF AN ARTICULATED STRUCTURE AND OF A SET OF REFERENCE FRAMES OF INTEREST DISPOSED ON SAID STRUCTURE

CROSS-REFERENCE TO RELATED APPLICATIONS

This application is the National Stage of International Application No. PCT/EP2013/054563, filed on Mar. 7, 2013, which claims the benefit of French Application No. 1252101, filed Mar. 8, 2012. The contents of all of these applications are incorporated herein by reference.

BACKGROUND

1. Technical Field

Various embodiments relate to a method of identifying geometric parameters of an articulated structure and of an assembly of reference frames of interest disposed on said structure, with the aid of a tailored system of measurements.

The information evaluated can be the following:

The positions and orientations of the reference frames of interest with respect to the structure;

The biomechanical parameters of the articulated structure (for example the lengths of the segments).

Various embodiments of the invention are applicable, for example, without this list being limiting, to the following functions:

Accurately characterizing a system of measurements applied to the articulated structure. The reference frames of interest are then those of the measurement devices which instrument the structure.

Measuring the kinetic parameters of a solid structure (articulated or not). The reference frames of interest are generally the points where one is interested in the kinetic parameters.

Capturing the motion of an articulated body (sectors of medicine, animation cinema, sport or else video games, research in biomechanical analysis, in robotics, etc.).

2. Description of the Related Art

The fields of application in which articulated structures are used are expanding. It is possible to cite, for example, robotics and human or animal biomechanics. In these sectors, two types of information are of importance:

The geometry of the articulated structure; and

The position and the orientation of an assembly of reference frames of interest (where for example temperature measurements, kinetic measurements, etc. have been made available).

SUMMARY OF THE INVENTION

Various embodiments propose to treat these two problem areas jointly without resorting to the methods of the prior art, which principally consist in directly measuring the lengths of the segments of the articulated structure (for example, with the aid of a tape measure or with the aid of a complex optical system, etc.), in taking into account a morphological model making it possible to simulate the dynamics of said articulated structure and in locating the reference frames of interest on the segments also by direct measurement of their position and orientation.

Various embodiment methods include associating a system of measurements distributed over said structure, said system comprising sensors fixed securely to the segment of said structure at the site of the points of the reference frames of interest so as to extract therefrom the desired information described hereinabove.

Hereinafter in the document, we will illustrate embodiments of the invention principally in an exemplary application in which:

The articulated structure is biomechanical and it is desired to evaluate the length of its segments;

A motion measurements system is disposed on the articulated structure and it is desired to identify their position and orientation, the previously defined reference frames of interest are those of each measurement element of the system; this system serves at one and the same time for the measurement of the motion and for the identification of the geometric parameters making it possible to characterize the segments of the structure and the position of reference frames of interest with respect to them;

Said measurements system comprises at least one accelerometer.

For this purpose, various embodiment methods of determining the position of an assembly of sensors in a reference frame tied to a segment of an articulated chain are disclosed, in which the assembly of sensors comprises at least one accelerometer and is secured to said articulated chain, the method comprising: a first step of determining an orientation of a reference frame tied to the assembly of sensors with respect to the reference frame tied to said segment for at least one chosen configuration of said articulated chain; a second step of estimating a motion of said reference frame tied to the assembly of sensors in a terrestrial reference frame in the course of at least one motion of said segment; a third step of calculating said position of said assembly of sensors in the reference frame tied to said segment, said third step receiving as input the estimation of the motion of said reference frame tied to the sensor as output by the second step and the measurements of said accelerometer in the course of said at least one motion.

Advantageously, the first step comprises a first sub-step of calculating a first switching matrix for passing from said reference frame tied to the assembly of sensors to a reference frame tied to the earth and a second sub-step of calculating a second switching matrix for passing from said reference frame tied to the earth to a reference frame tied to said segment.

Advantageously, the first calculation sub-step uses at least one measurement of at least one second sensor of said assembly of sensors, said second sensor being able to provide measurements of at least one physical field which is substantially uniform over time and in space or of rotation speed.

Advantageously, the first calculation step furthermore comprises a calculation sub-step prior to said first sub-step in the course of which a third switching matrix for passing between a reference frame in motion and said reference frame tied to the earth is calculated, said third switching matrix being either chosen or determined on the basis of measurements of at least one physical field which is substantially uniform over time and in space or of the measurements of the rotation speed of said reference frame in motion with respect to said reference frame tied to the earth.

Advantageously, the first step is performed for at least two configurations of said articulated chain.

Advantageously, prior to the first step, a first sub-step of determining a substantially invariant axis of rotation of said segment is carried out.

Advantageously, the second step uses the outputs of at least one sensor chosen from the group comprising the accelerometer and a second sensor of said assembly of sensors, said second sensor being able to provide measurements of at least one physical field which is substantially uniform over time and in space or of rotation speed.

Advantageously, in the course of the second step, said at least one motion of the segment is a rotation around a substantially invariant axis.

Advantageously, in the course of at least the second and third steps, use is made of a predictive model of the outputs of the accelerometer chosen as a function of the type of the motion of said segment and the position is calculated of said assembly of sensors on said segment as output by an algorithm minimizing the errors between measured values and predicted values.

Advantageously, said articulated chain comprises at least N segments, N being greater than or equal to two.

Advantageously, a specific embodiment method further comprises a step in the course of which the length of at least one segment of said articulated chain is calculated.

Advantageously, the calculation of a segment i inserted into an articulated chain comprising j segments, j being greater than 1 and than i, is performed by solving the equation $Mat\_tot_{mvt} * PosLong = Acc_{basis-free}(t_{initial} \rightarrow t_{final})$ in which:

$Mat\_tot_{mvt}$ is a matrix of dimension (i, j) whose coefficients are calculated by $$Mat_{mvt}(t, sensor\ j, sensor\ i) = \left[ -\left(\frac{\partial_1^{Sensori}Rotation(t)Earth}{\partial t^2}\right)_{reference\ frame\ sensor\ j} \right]$$

$$PosLong = \begin{bmatrix} Position_{sensor 1} \\ Position\ origin_{segment\ 2} \\ Position_{sensor\ 2} \\ \vdots \\ Position\ origin_{segment\ N} \\ Position_{sensor\ N} \end{bmatrix}$$

$PosLong$ is the vector

The basis-free acceleration at the instant t is calculated by the formula $$Acc_{basis-free}(t) = Meas_{Acc}(t) - G0_{reference\ frame\ sensor} + Acc_{assembly_{referenceframesensor}}$$

Advantageously, said articulated chain is a part of a human body or of a humanoid structure.

Advantageously, the configurations of said articulated chain are determined by execution of at least N predefined successive gestures, each gesture enabling only a rotation of all or some of the segments of said chain in a unique plane about a unique axis passing through an articulation linking two segments, the segments other than the two stated segments remaining aligned during said rotation, in such a way that rotations of segments are executed about at least N distinct axes.

Advantageously, N is greater than or equal to 3, a first segment corresponding to a shoulder, a second segment corresponding to an arm linked to the shoulder and a third segment corresponding to a forearm linked to the arm by an elbow, the execution of predefined gestures including, in this order: a rotation of the entire body about a vertical axis (105) that may be regarded as the axis of the body, the shoulder-arm-forearm assembly being held outstretched in a horizontal plane during the rotation of the body about said axis, and; a rotation of the arm-forearm assembly about a horizontal axis (205) passing through the articulation linking the shoulder to the arm, the arm-forearm assembly being held outstretched during said rotation, and; a rotation of the forearm about a horizontal axis (305) passing through the elbow linking the arm to the forearm, the shoulder-arm assembly being held outstretched during said rotation.

Advantageously, each rotation of segments is executed about an axis passing through an articulation.

Various embodiments also disclose a system for determining the position of an assembly of sensors in a reference frame tied to a segment of an articulated chain, said assembly of sensors comprising at least one accelerometer and being secured to said articulated chain, said system comprising a first module for determining an orientation of a reference frame tied to the assembly of sensors to said reference frame tied to said segment for at least one configuration of said articulated chain; a second module for estimating a motion of said reference frame tied to the assembly of sensors in a terrestrial reference frame in the course of at least one motion of said segment; a third module for calculating said position of said assembly of sensors in the reference frame tied to said segment, said third module receiving as input the estimation of the motion of said reference frame tied to the sensor as output by the second module and the measurements of said accelerometer in the course of said at least one motion.

The principal advantage of certain embodiments is that of identifying, in an accurate, automatic, fast and practical manner, critical geometric parameters of an articulated structure and of a plurality of reference frames of interest. In some of its embodiments, the invention is particularly advantageous since it expresses the estimation of said parameters in the form of a linear least squares problem, the calculation of the estimate is therefore explicit and optimal.

BRIEF DESCRIPTION OF THE DRAWINGS

Other characteristics and advantages of the invention will become apparent with the aid of the description which follows offered with regard to the following figures which illustrate examples of implementation of the method according to certain non-limiting embodiments of the present invention.

DETAILED DESCRIPTION OF THE PREFERRED EMBODIMENTS

An articulated structure is composed of at least one first segment which can be mobile in space. The following segments are attached one following the other in the form of a tree possibly comprising several branches.

The system of measurements comprises sensors, disposed on the segments of the articulated structure, whose reference frames are the reference frames of interest.

Various embodiments are aimed at a method utilizing:
Means for measuring the orientation of the reference frames of interest, sensors of the system of measurements or segments,
The sensors worn of the system of measurements comprising at least one accelerometer,
Gestures to be performed;
so as to extract therefrom:
The position and the orientation of the reference frames of interest on each segment,
If appropriate, the length of each segment.

Figure 1:
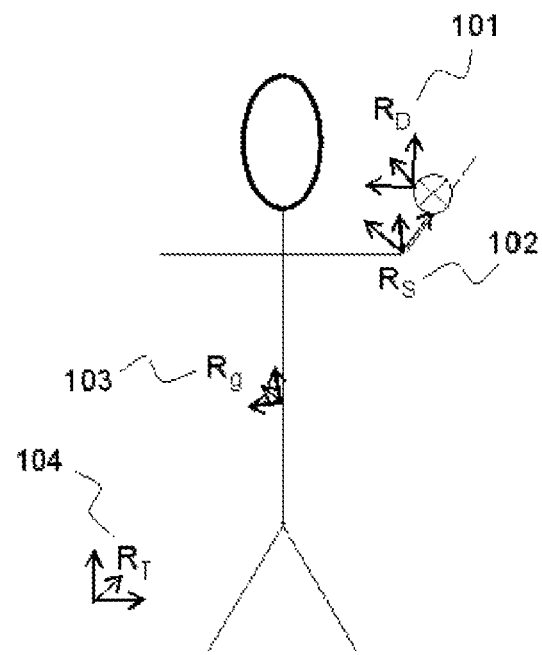
FIG. 1 specifies the reference frames used in the description of the present invention.

FIG. 1 specifies the reference frames used in a description of specific embodiments.

$R_D$ is the reference frame of interest, 101. The sensors making it possible to perform the measurements will be placed on the reference frame of interest, at least for the time of the measurement. In the subsequent description, the expressions "reference frame of interest" or "reference frame tied to the assembly of sensors" will be used alternatively to designate the reference 101.

$R_S$ is the reference frame tied to the segment, 102.

$R_g$ is the reference frame tied to the center of gravity of the body, 103.

$R_T$ is the fixed reference frame, 104. The fixed reference frame is for example tied to the Earth.

Figure 2:
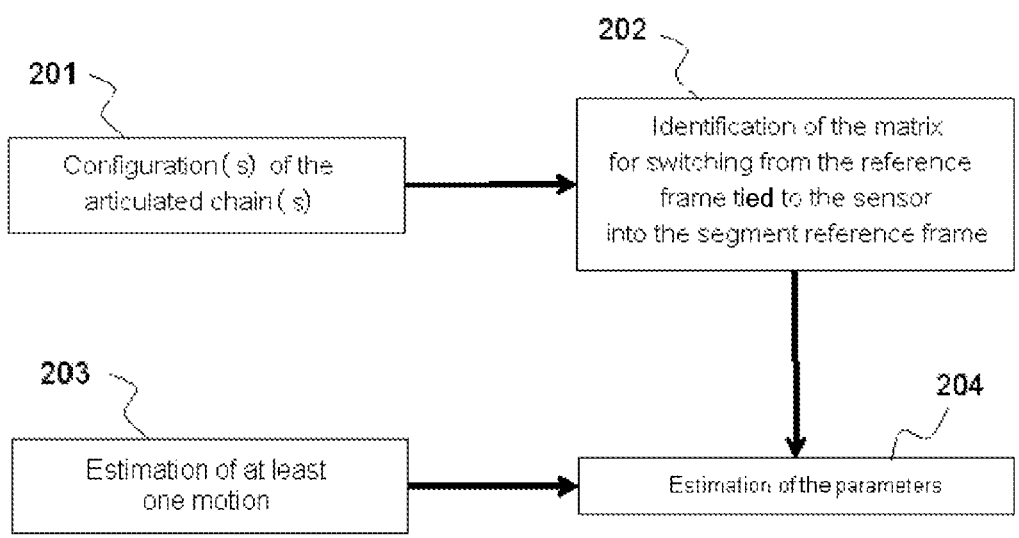
FIG. 2 represents a general flowchart of the processing operations in several embodiments of the invention.

FIG. 2 represents a general flowchart of the processing operations in several embodiments of the invention.

This entails determining the parameters which characterize the position and the orientation of the reference frames of interest with respect to the segments which constitute the branches of the articulated structure.

Accordingly, it is desirable firstly to determine the orientation of the reference frame tied to the assembly of sensors (or reference frame of interest), 101 with respect to the reference frame of the segment 102. This orientation can be a directly accessible data item or it can be determined in one or more configurations of the articulated structure, as illustrated further on in the description.

The articulated structure is also made to perform at least one more or less simple motion, so as to obtain measurements of the parameters of orientation and of position of the reference frame tied to the assembly of sensors employed, so as to solve the equation for the motions which are performed and to deduce therefrom the estimation of the parameters which characterize the position of the assembly of sensors in the reference frame of the segment.

Figure 4:
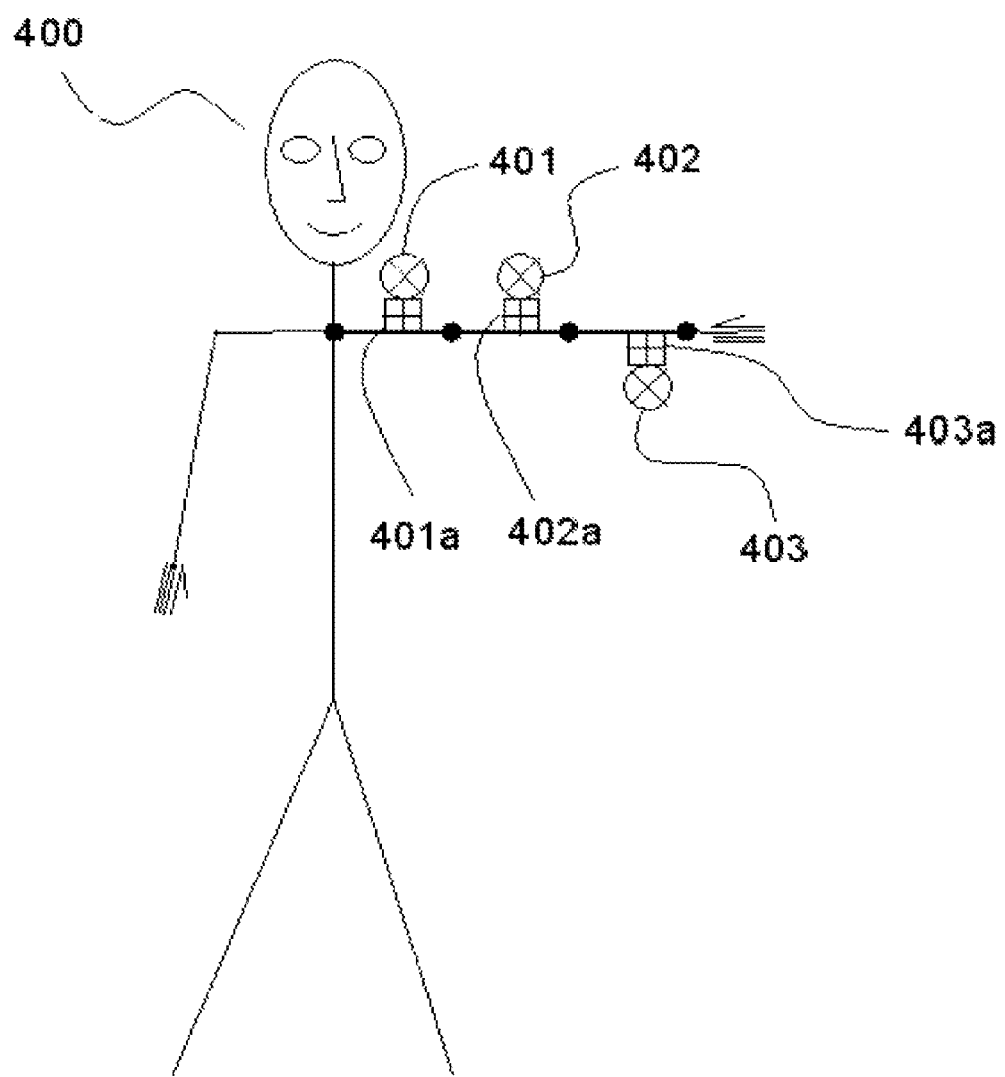
FIG. 4 illustrates the articulated structure (human being in the figure) equipped with an assembly of devices and with the associated system of measurements which will make it possible to identify the geometric parameters of the structure and devices whose reference frames are the reference frames of interest.

Thus, according to an embodiment of the invention, in the course of a first step 201, 202, one may fix the orientation of the sensor assembly directly in the reference frame of the segment 103, or one may determine the orientation of the assembly of sensors (for example the references 401, 401a, 402, 402a, 403, 403a of FIG. 4) in the reference frame the fixed reference frame, 104, by making the articulated structure take one or more configurations, which make it possible to determine said orientation, and therefore a switching matrix for passing between the reference frame 101 and the reference frame 104, and then a switching matrix for passing from the reference frame 104 to the reference frame 102 is determined.

Thereafter, in an embodiment, in the course of a step 203, the articulated structure is made to perform at least one motion for which it is possible to determine a predictive model of the measurements of the sensors belonging to the assembly of sensors 401, 401a, 402, 402a, 403, 403a.

Alternative variants for carrying out steps 201 and 203 are illustrated in the subsequent description.

Figure 3A:
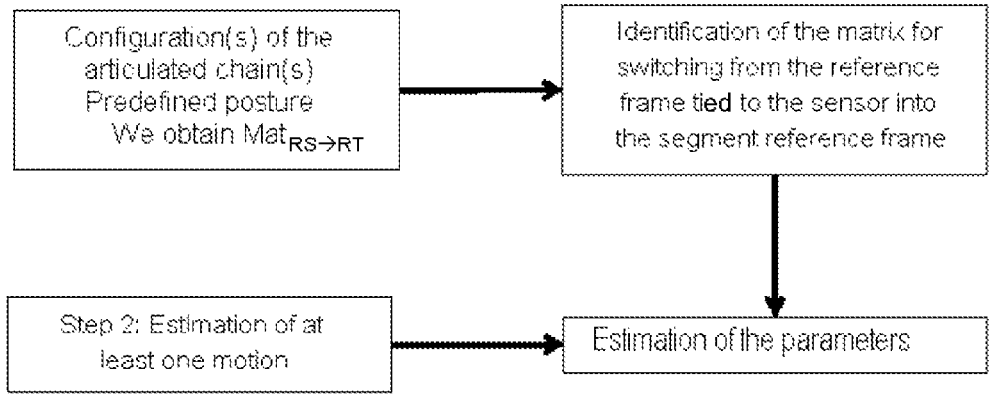
FIGS. 3*a* to 3*e* represent alternative variants of the invention in several of its embodiments.

In FIG. 3a is represented the flowchart of the processing operations of FIG. 2 in a first embodiment.

The assembly of sensors (references 401, 401a, 402, 402a, 403, 403a of FIG. 4) comprises a means for measuring the orientation $Mat_{RD\_RT}$ of the reference frames of interest 101 with respect to the fixed reference frame tied to the Earth ($R_T$, 104). Various sensors are capable of providing measurements with respect to fields that are substantially invariant over time and in space (gravity, the terrestrial magnetic field) or else with respect to a fixed reference in the reference frame 104, such as magnetic, optical, acoustic or radiofrequency sensors positioned in the assembly of sensors or on a fixed base in conjunction with a fixed base with respect to the reference frame 104 or with sensors positioned in the assembly of sensors. For example, gyrometers are capable of providing this information. Magnetometers are also capable of playing this role, as are optical, acoustic or radiofrequency means.

In this case, the first step 201, 202 which makes it possible to identify the target matrix $Mat_{RD\_RS}$ includes adopting postures or poses that are predefined and therefore, known in the guise of $Mat_{RD\_RT}$ and therefore, by transitivity of the rotation matrices the matrix $Mat_{RD\_RS}$:

$$Mat_{RD\_RS} = Mat_{RD\_RT} \times (Mat_{RS\_RT})^{-1}$$

The second step 203 includes performing gestures and in analyzing the accelerometric measurement by utilizing the knowledge of $Mat_{RD\_RT}$ and $Mat_{RD\_RS}$ so as to estimate the parameters of lengths and distances, by applying the composition law for motions which links the accelerations of the various points concerned.

The third step 204 of estimating the parameters for the position of the assembly of sensors on the segment is explained further on in the description.

Figure 3B:
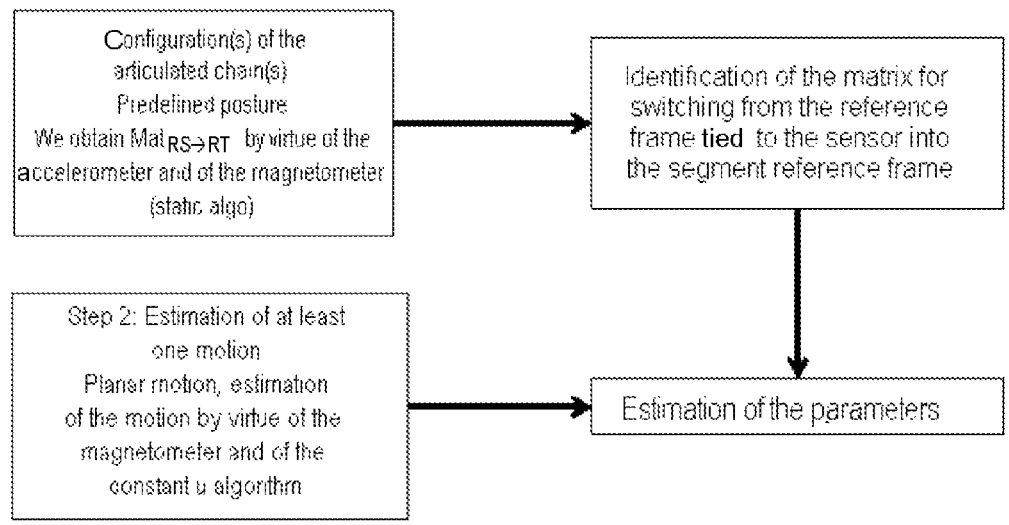

Certain particular cases, illustrated by the flowchart of the processing operations of FIG. 3b, suggest the addition of constraints on the type of motions. For example, employing magnetometers as means for measuring the orientations may constrain the gestures to comply with a substantially invariant axis of rotation. A so-called "U constant" algorithm is then used to solve the equations for the motions as explained further on in the description. Such an algorithm is disclosed in application EP1985233 belonging to the applicants of the present application, which is incorporated herein by reference. The configurations and motions which the articulated structure is to be made to perform are illustrated in the embodiments described as commentary to FIGS. 5, 6 and 7.

Figure 3C:
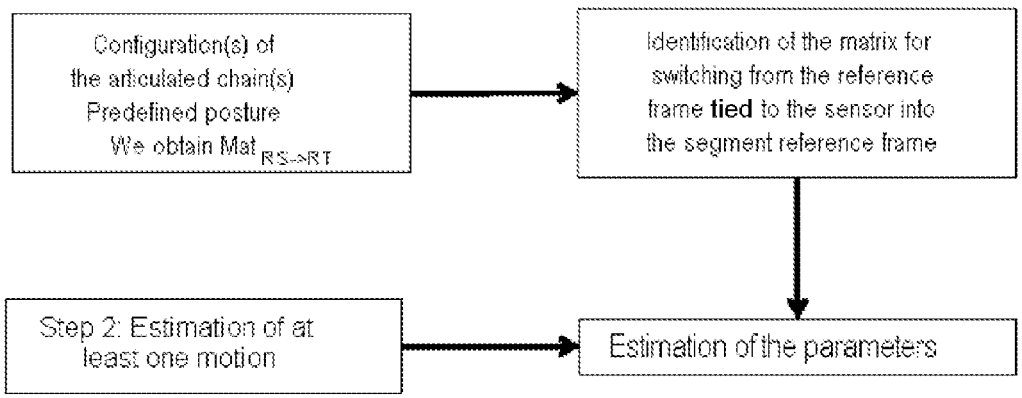

FIG. 3c represents the flowchart of the processing operations of a 2$^{nd}$ embodiment in which a means is available for measuring the orientation $Mat_{RD\_R'}$, R' being an arbitrary reference frame whose motion in the fixed reference frame $R_T$ is known or that it is possible to fix. This allows us to return to the previous case for steps 203 and 204. For example, a system of directional antennas worn on the one hand at the level of the center of mass (R'), and on the other hand at the level of the reference frames of interest, makes it possible to follow the motions of the reference frame R' with respect to the reference frame of the earth, 104.

Figure 3D:
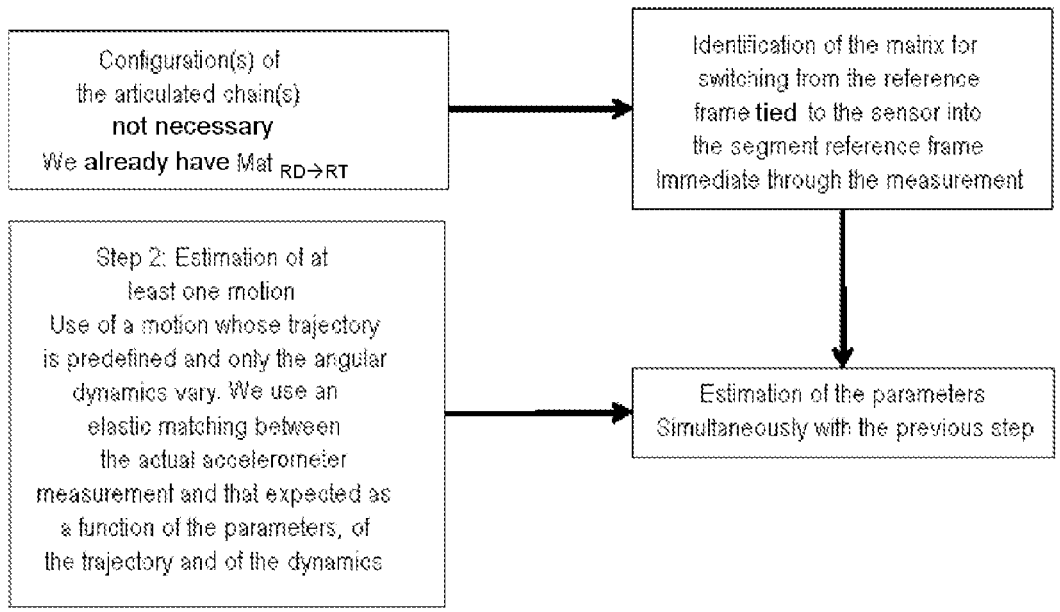

FIG. 3d represents the flowchart of the processing operations of a 3$^{rd}$ embodiment in which the orientation of the reference frame 101 in the reference frame 102 is already available, where a means of measuring said orientation is available. A matrix $Mat_{RD\_RS}$ is then determined which makes it possible to pass directly from the reference frame of interest to the reference frame of the segment, thereby carrying out the first step 201, 202 of the method of the invention. For example, it is possible to use the means cited in patent application EP1985233 belonging to the applicants of the present application, already cited. These means may comprise just an accelerometer or, in fact the same sensors as those of the system of measurements of embodiments of the invention. According to various embodiments, at least two substantially invariant axes of rotation of the segment instrumented with the sensor or sensors are determined. The rotation motions are determined as substantially invariant with respect to one or more thresholds chosen by the user of the system.

The second step 203 includes performing protocol motions, for which it is desirable to impose the trajectory of all the equipped segments (X,Y,Z) independently of time or of the execution speed profile. The accelerometric data item measured in the course of time during this gesture is then compared elastically (elastic deformation of time) with the expected measurement model tied to the predefined trajectory for example by an error minimization operation or likelihood ratio maximization operation whose variables are the parameters sought.

The third step 204 (which may, if appropriate, be simultaneous with step 203) of estimating the parameters for the position of the assembly of sensors on the segment is explained further on in the description.

Figure 3E:
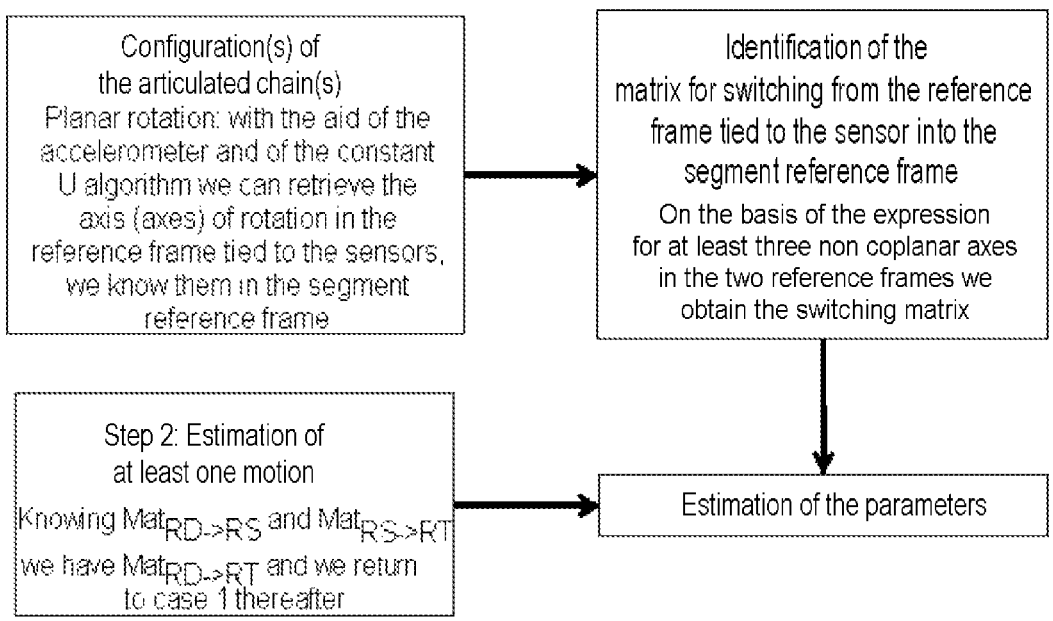

FIG. 3e represents a flowchart of the processing operations of a 4$^{th}$ embodiment of the invention in which a means is available for measuring the orientation $Mat_{RS\_RT}$ of the segment in the fixed reference frame tied to the Earth, 103. The same means as those used in the embodiment of FIG. 3a may be suitable, for example, optical systems, ultrasound systems or any other system which has a fixed base in the reference frame tied to the Earth.

The first step 201, 202 includes performing protocol motions, with substantially invariant axis of rotation, so that with the aid of a measurement system comprising at least one accelerometer, it is possible to identify the rotation matrix $Mat_{RD\_RT}$ and thus return to the first case hereinabove.

The third step 204 of estimating the parameters for the position of the assembly of sensors on the segment is explained further on in the description.

FIG. 4 illustrates a particular case where the articulated structure (400) is a human being who is equipped on a part only of their body: left shoulder and arm. The shoulder as well as the arm and the forearm are equipped respectively with the devices (401a, 402b, 403b) and, at the same locations the sensors of said system of measurements (401, 402, 403).

Figure 5:
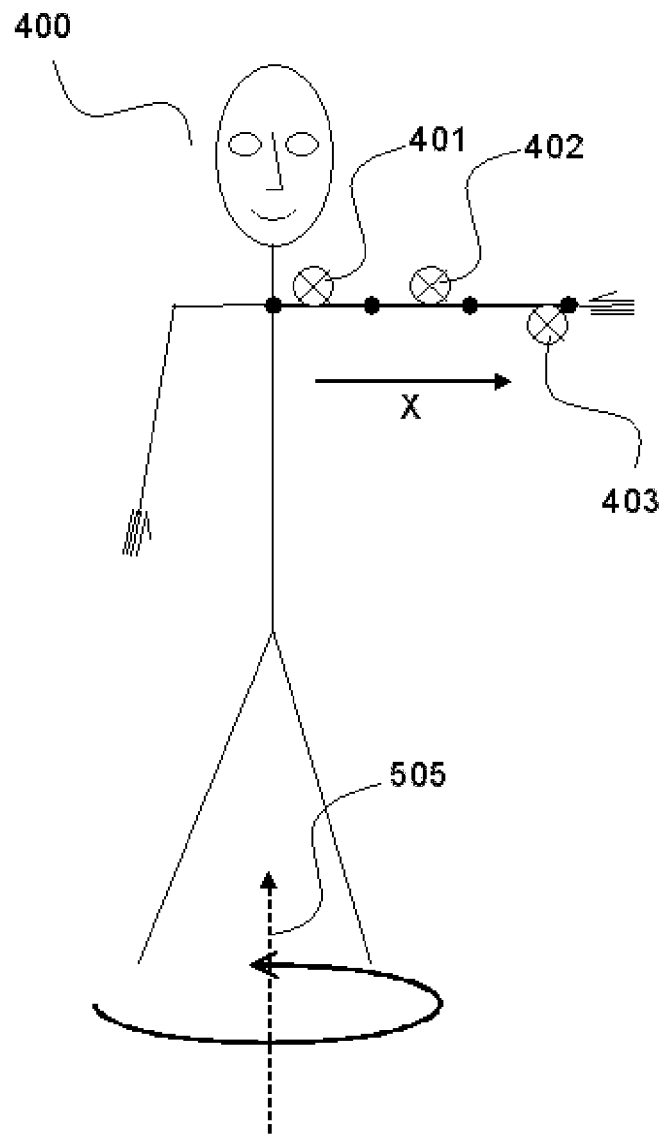
FIG. 5 illustrates a first motion of a human being wearing sensors of a measurement system whose reference frames are the reference frames of interest, in an embodiment of the invention.

FIG. 5 illustrates a first motion of a human being wearing sensors (401, 402, 403) of a measurement system, in an embodiment of the invention. In this embodiment, the assembly of devices represented in FIG. 4 and the system of measurements are merged and consist of sensors which associate accelerometers and magnetometers (Embodiment illustrated in FIG. 3b).

This exemplary implementation of the invention makes it possible to calibrate an assembly of three sensors 401, 402 and 403 tied to three segments, namely the shoulder of a person, to which the sensor 401 is attached, the arm of the person, to which the sensor 402 is attached, and finally the forearm of the person, to which the sensor 403 is attached. For the present exemplary embodiment of the invention, the applicants have used sensors 401, 402 and 403 marketed by one of the applicants under the commercial name Motion-Pod and which each combine a three-axis accelerometer with a three-axis magnetometer. Each of the sensors 401, 402 and 403 transmits its data via a radio link to a box commonly called a Motion Controller, this box being linked to a computer by a USB link. The box and the computer are not represented in the figure. The data are utilizable on the computer by virtue of a programming interface marketed by the applicants under the commercial name Smart Motion Development Kit (SMDK). The SMDK programming interface makes it possible either to obtain raw and calibrated measurements of a MotionPod, or to obtain an estimation of the orientation of a MotionPod.

Hereinafter, the terms sensor, or MotionPod will be used interchangeably to designate the elements 401, 402 and 403 represented in FIGS. 4, 5, 6 and 7.

Prior to the use of the system thus including the sensors 401, 402 and 403, for example to capture the motions of the assembly with three segments shoulder-arm-forearm of the person, it is desirable to evaluate the change of reference frame between the reference frame of the solid that constitutes each segment and the reference frame of the sensor attached to said segment. Thus, it is desirable to evaluate the change of reference frame between the reference frame of the shoulder and the sensor 401, the change of reference frame between the reference frame of the arm and the sensor 402, as well as the change of reference frame between the reference frame of the forearm and the sensor 403. It is also desirable to evaluate the changes of reference frame between the various segments. This is an object of the method of identifying the geometric parameters according various embodiments of the invention. In the present exemplary embodiment, this entails firstly evaluating the orientation of each of the sensors 401, 402 and 403 with respect to the segment to which said sensor is attached by using the means for measuring the orientation and optionally protocol gestures (see the various embodiments described hereinabove as commentary to FIGS. 3a to 3e). Thereafter it entails evaluating the position of each of the sensors 401, 402 and 403 with respect to the segment to which said sensor is attached in the form of a position vector. It also entails evaluating the length of each of the three segments in the form of a length vector. It should be noted that the position of the sensors could be measured with a rule, but the estimation obtained may turn out to be too coarse; furthermore, only the component, referenced X in FIGS. 5, 6 and 7, along the length of each of the segments can actually be evaluated by this manual procedure.

The method of identifying the geometric parameters according to various embodiments of the invention comprises a step of evaluating the orientation of the sensors. In this exemplary embodiment (FIGS. 5, 6, 7), this entails notably giving the body a series of predefined static postures and comparing the actual measurements with theoretical values, so as to determine the orientation parameters. The larger the series, the better the accuracy. A single measurement is sufficient if the magnetic field is known perfectly and if the orientation of the segment is determined exactly, but this is not the case in human motions.

Thus, for example, the body is firstly placed in a posture termed "posture 1" which corresponds to the reference posture, that is to say with all the angles at 0. Next it is rotated (for example) 90° clockwise, to attain the posture termed "posture 2". It is then known that the sensors 401, 402 and 403 measure (the equations being valid for all these sensors):

$$MeasureAccelero_{Positive1} = \text{R\_orientation} * G0$$

$$MeasureMagneto_{Positive1} = \text{R\_orientation} * H0$$

$$MeasureAccelero_{Posture2} = \text{R\_orientation} * \begin{bmatrix} 0 & -1 & 0 \\ 1 & 0 & 0 \\ 0 & 0 & 1 \end{bmatrix} * G0$$

$$MeasureMagneto_{Posture2} = \text{R\_orientation} * \begin{bmatrix} 0 & -1 & 0 \\ 1 & 0 & 0 \\ 0 & 0 & 1 \end{bmatrix} * H0$$

Where:
MeasureAccelero$_{Posture\ k}$ designates a measurement taken by the accelerometer when the body occupies the posture k∈{1,2};
MeasureMagneto$_{Posture\ k}$ designates a measurement taken by the magnetometer when the body occupies the posture k∈{1,2};
$\vec{G}$ a designates the terrestrial gravitational field;
$\vec{H}$ designates the terrestrial magnetic field;
(GH) designates the angle between $\vec{G}$ and $\vec{H}$;

$$G0 = \begin{bmatrix} 0 \\ 0 \\ 1 \end{bmatrix}$$

and $$H0 = \begin{bmatrix} \sin(GH) \\ 0 \\ \cos(GH) \end{bmatrix}$$

respectively designate the values of the fields $\vec{G}$ and $\vec{H}$ in a given initial position and measured in the reference frame of the sensor;
R_orientation designates the rotation matrix to be identified.

Indeed, by convention the Z axis is vertical and is oriented downwards. Several quantities may be determined: the orientation matrix R_orientation and the values of sin(GH) and cos(GH). Accordingly, the following calculations can be performed:

$$MeasureAccelero_{Posture1} = \frac{MeasureAccelero_{Posture1}}{\|MeasureAccelero_{Posture1}\|}$$

$$MeasureAccelero_{Posture2} = \frac{MeasureAccelero_{Posture2}}{\|MeasureAccelero_{Posture2}\|}$$

$$MeasureMagneto_{Posture1} = \frac{MeasureMagneto_{posture\ 1}}{\|MeasureMagneto_{Posture1}\|}$$

$$MeasureMagneto_{Posture2} = \frac{MeasureAccelero_{Posture2}}{\|MeasureAccelero_{Posture2}\|}$$

This yields:

sin(GH)=mean(‖MeasureAccelero$_{Posture\ 1}$×MeasureMagneto$_{Posture\ 1}$‖,‖MeasureAccelero$_{Posture\ 1}$×MeasureMagneto$_{Posture\ 2}$‖)

cos(GH)=mean(MeasureAccelero$_{Posture\ 1}$□MeasureMagneto$_{Posture\ 1}$,MeasureAccelero$_{Posture\ 2}$□MeasureMagneto$_{Posture\ 2}$)

It is noted that the first expression (sin(GH)) is a mean of the vector products of the measurements of the sensors used and that the second expression (cos(GH)) is a mean of the scalar products of the measurements of the sensors used.

Finally, the rotation matrix R_orientation is determined by:

Mat = [MeasureAccelero$_{Posture\ 1}$, MeasureMagneto$_{Posture\ 1}$, MeasureMagneto$_{Posture\ 2}$]

$$\text{R\_orientation} = Mat * \begin{bmatrix} 0 & \sin(GH) & 0 \\ 0 & 0 & -\sin(GH) \\ 1 & \cos(GH) & \cos(GH) \end{bmatrix}^{-1}$$

This data item is then included in the model of measurements of the sensors in triplet angle form.

To proceed with the identification of the geometric parameters in this embodiment, a step is carried out of evaluating the lengths of the segments and positions of the sensors on the segments by virtue of a protocol of gestures. This step can rely on an algorithm aimed at reducing the number of degrees of freedom by enabling only planar rotations in relation to constant axes, doing thus so as to utilize the a priori knowledge of the constant vector to solve the system.

Initially, the method for detecting a substantially invariant axis of rotation, described in patent EP1985233 already cited, makes it possible, using solely the measurements of the magnetometers under the planar motion condition to which the structure of the sensors is constrained, to retrieve the motion, that is to say to deduce the axis of rotation in the reference frame of the magnetometer and of the accelerometer, and also to deduce the angle of rotation. This makes it possible to validate the evaluation of the orientation of the sensors performed at the previous step and even to refine it. This also makes it possible to verify that the orientation of the various sensors is indeed the same, that is to say that the axis of rotation calculated on the basis of the measurements of the accelerometer is identical to that calculated on the basis of the measurements of the magnetometer undergoing the same planar motion. If such is not the case, it is desirable to perform an identification of the box geometric parameters, that is to say an identification of the geometric parameters that relate to the relative orientation of the magnetometer and of the accelerometer.

Subsequently, the measurements of the accelerometers are used to determine the distance from each sensor to the axis of rotation. The measurements are transformed into the reference frame expected by virtue of the orientation matrices evaluated during the previous step, doing thus so as to work with respect to the segments of the body and not with respect to the sensors. The identification of the geometric parameters are preferably done in the order in which they are described in the present exemplary embodiment. The axes of rotation naturally pass through the articulations of the body. It is therefore desirable to define a protocol to excite sufficient axes so as to determine the three components of the length and position vectors.

FIG. 5 illustrates a rotation of the entire body about a vertical axis 505 that may be regarded as the axis of the body, the shoulder-arm-forearm assembly being held outstretched in a horizontal plane during the rotation of the body about the axis A1. We define:

$$\theta_a = \underset{i=1,2,3}{\text{mean}}(Uconstant(Mag_i))$$

$$\dot{\theta}_a = \frac{d\theta_a}{dt}$$

Where:
$Mag_i$ designates the measurement taken by the magnetometer of the sensor $i \in \{1, 2, 3\}$;
Uconstant designates a function which returns the axis of rotation obtained by the method described in patent EP1985233 already cited;
mean designates a function which returns the arithmetic mean.

We then have, for i=1, 2, 3:

$$\text{MeasureAccelero}_{X,i}{}^a = R_i * \dot{\theta}_a{}^2$$

Where:

$$\begin{cases} R_1 = \text{distance(basis shoulder, } sensor_1)_X \\ R_2 = \text{distance(basis shoulder, } sensor_2)_X \\ \quad = \text{length (shoulder)}_X + \text{distance(basis arm, } sensor_2)_X \\ R_3 = \text{distance(basis shoulder, } sensor_3)_X \\ \quad = \text{length (shoulder)}_X + \text{length (arm)}_X + \text{distance(elbow, } sensor_3)_X \end{cases}$$

Figure 6:
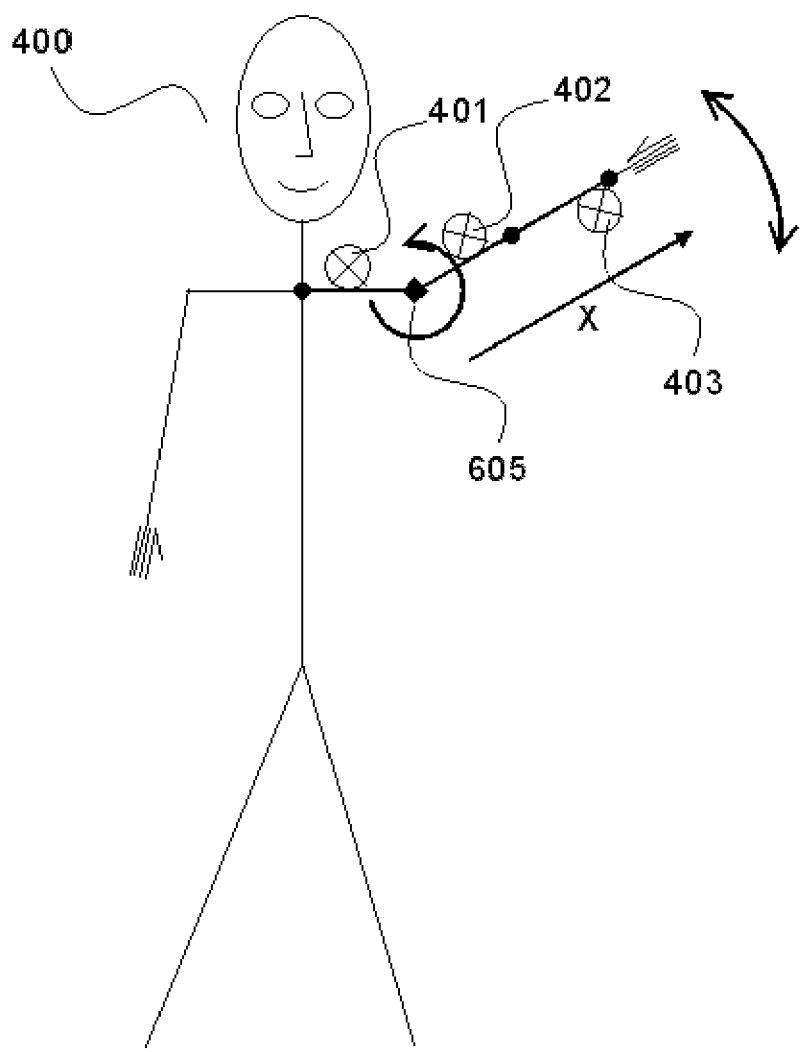
FIG. 6 illustrates a second motion of a human being wearing sensors of a measurement system whose reference frames are the reference frames of interest, in an embodiment of the invention.

FIG. 6 illustrates a rotation of the arm-forearm assembly about a horizontal axis 605, perpendicular to the plane of the figure and passing through the articulation linking the shoulder to the arm, the arm-forearm assembly being held outstretched during the rotation. We define:

$$\theta_b = \underset{i=2,3}{\text{mean}}(Uconstant(Mag_i))$$

$$\dot{\theta}_b = \frac{d\theta_b}{dt}$$

We then have, for i=2, 3:

$$\text{MeasureAccelero}_{X,i}{}^b = R_i * \dot{\theta}_b{}^2 + G * \sin(\theta_b)$$

With:

$$\begin{cases} R_2 = \text{distance(basis arm, } sensor_2)_X \\ R_3 = \text{distance(basis arm, } sensor_3)_X \\ \quad = \text{length (arm)}_X + \text{distance(elbow, } sensor_3)_X \end{cases}$$

Figure 7:
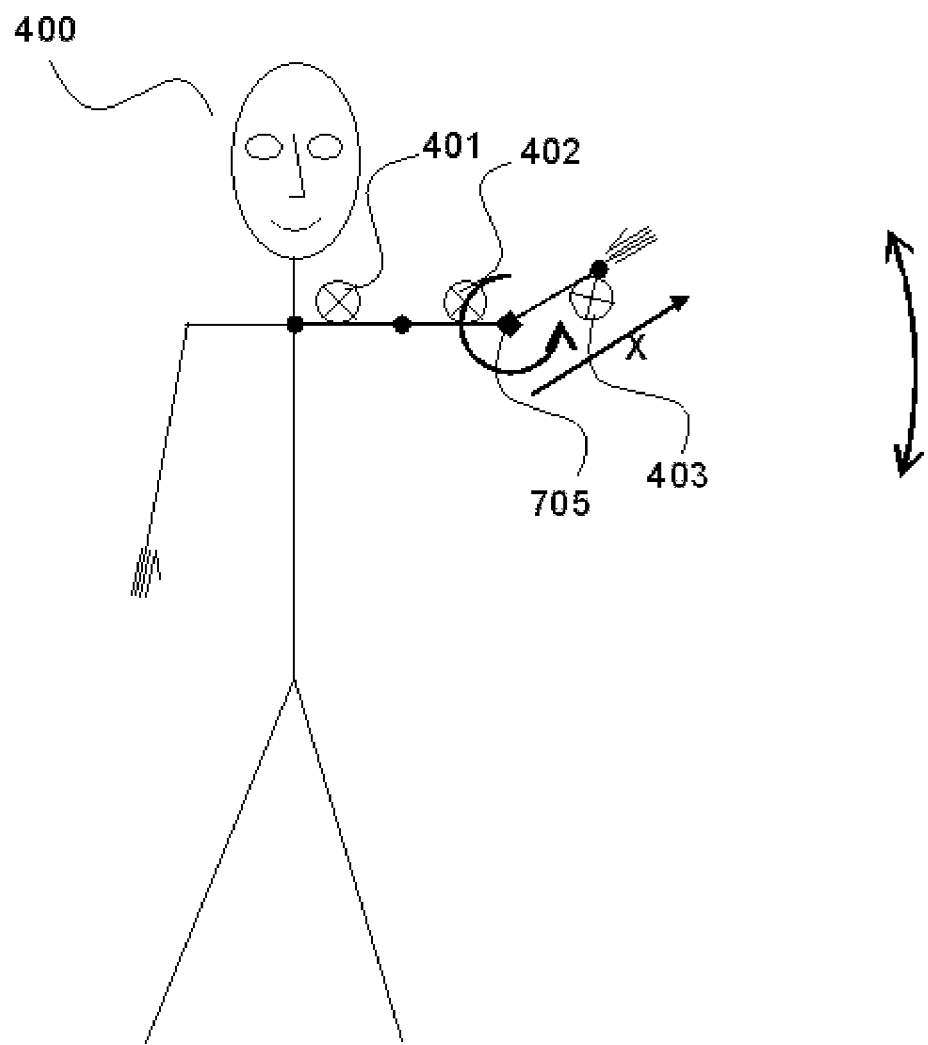
FIG. 7 illustrates a third motion of a human being wearing sensors of a measurement system whose reference frames are the reference frames of interest, in an embodiment of the invention.

FIG. 7 illustrates a rotation of the forearm about a horizontal axis 705, perpendicular to the plane of the figure and passing through the articulation linking the arm to the forearm, that is to say the elbow, the shoulder-arm assembly being held outstretched during the rotation. We define:

$$\theta_c = \underset{i=3}{\text{mean}}(Uconstant(Mag_i))$$

$$\dot{\theta}_c = \frac{d\theta_c}{dt}$$

We then have:

$$\text{MeasureAccelero}_{X,3} R_3 * \dot{\theta}_c{}^2 + G * \sin(\theta_c)$$

With:

$$R_3 = \text{distance(elbow, } sensor_3)_X$$

Using the relations hereinabove, the following equations can be deduced:

$$\begin{cases} \text{Position}_{X,1} = \text{distance(basis shoulder, } sensor_1)_X = \left(\frac{\text{MeasureAccelero}_{X,1}^a}{\dot{\theta}_a^2}\right) \\ \text{Position}_{X,2} = \text{distance(basis arm, } sensor_2)_X = \left(\frac{\text{MeasureAccelero}_{X,1}^b - \sin(\theta_b) * G}{\dot{\theta}_b^2}\right) \\ \text{Position}_{X,3} = \text{distance(elbow, } sensor_3)_X = \left(\frac{\text{MeasureAccelero}_{X,1}^c - \sin(\theta_c) * G}{\dot{\theta}_c^2}\right) \end{cases}$$

Finally, the lengths of the segments can be estimated according to the X component:

$$\begin{cases} \text{Length}_{X3} = \text{Length(shoulder)}_X = \text{distance(basis shoulder, base arm)}_X \\ \quad = \left(\frac{\text{MeasureAccelero}_{X,2}^a}{\dot{\theta}_a^2} - \text{Position}_{X,2}\right) \\ \text{Length}_{X,2} = \text{length(arm)}_X = \text{distance(basis arm, elbow)}_X \\ \quad = \left(\frac{\text{MeasureAccelro}_{X3}^a}{\dot{\theta}_a^2} - \text{Length}_{X3} - \text{Position}_{X,3}\right) \\ \quad = \left(\frac{\text{MeasureAccelero}_{X3}^b}{\dot{\theta}_b^2} - \text{Position}_{X,3}\right) \end{cases}$$

For the second length, it is preferable to evaluate the mean of the two equations hereinabove to improve the quality of the estimation.

The same may be undertaken on the other axes of the body, so as to define the other components of the length and position vectors.

While remaining entirely within the framework of the present invention, it is also possible to make the articulated structure perform less constrained motions than those used in the embodiments of FIGS. 5, 6 and 7. In these cases, it may not be possible to apply the simplified predictive models, used in these embodiments, of the measurements. It will, however, be possible to apply the various steps of embodiments of the method, it being understood that the 3$^{rd}$ step of the method for estimating the parameters may call upon a more complex predictive model of the measurements, for example that described in the patent application filed on the same day as the present application by the same applicants having the same inventor and having as title "PROCEDE D'IDENTIFICATION DES PARAMETRES GEOMETRIQUES D'UNE STRUCTURE ARTICULEE ET D'UN ENSEMBLE DE REPERES D'INTERET DISPOSES SUR LADITE STRUCTURE" [METHOD OF IDENTIFYING THE GEOMETRIC PARAMETERS OF AN ARTICULATED STRUCTURE AND OF AN ASSEMBLY OF REFERENCE FRAMES OF INTEREST DISPOSED ON SAID STRUCTURE], the contents of which are incorporated herein by reference. According to various embodiments of the invention, use is made of the measurements model represented by the following equation:

$$\text{Meas\_Acc} = {}^{Sensor}R_{Earth} * \left(G0 - \left(\frac{\partial^2 \, {}^{Earth}T_{Sensor}}{\partial t^2} + \text{Acc\_assembly}\right)\right)$$

Indeed, we have the accelerometric measurements meas_acc and the representation of the motion by virtue of step 2 of the present invention. We can therefore construct the vector $Acc_{basis\text{-}free}$ by virtue of the equality:

$$Acc_{basis\text{-}free}(t) = Meas_{Acc}(t) - G0_{\substack{reference \, frame \\ sensor}} + Acc_{\substack{assembly \, reference \, frame \\ sensor}}$$

We can also construct the matrix $\text{Mat\_tot}_{mvt}$ by virtue of the equality:

$$\text{Mat\_tot}_{mvt} = \begin{bmatrix} Mat_{mvt}(t_{initial}, \text{sensor } 1, \text{sensor } 1) & \cdots & Mat_{mvt}(t_{initial}, \text{sensor } 1, \text{sensor } N) \\ \vdots & \ddots & \vdots \\ Mat_{mvt}(t_{final}, \text{sensor } 1, \text{sensor } 1) & \cdots & Mat_{mvt}(t_{final}, \text{sensor } N, \text{sensor } N) \\ Mat_{mvt}(t_{initial}, \text{sensor } 2, \text{sensor } 1) & \cdots & Mat_{mvt}(t_{initial}, \text{sensor } 2, \text{sensor } N) \\ \vdots & \ddots & \vdots \\ Mat_{mvt}(t_{final}, \text{sensor } 2, \text{sensor } 1) & \cdots & Mat_{mvt}(t_{final}, \text{sensor } 2, \text{sensor } N) \\ \vdots & & \vdots \\ Mat_{mvt}(t_{initial}, \text{sensor } N, \text{sensor } 1) & \cdots & Mat_{mvt}(t_{initial}, \text{sensor } N, \text{sensor } N) \\ \vdots & \ddots & \vdots \\ Mat_{mvt}(t_{final}, \text{sensor } N, \text{sensor } 1) & \cdots & Mat_{mvt}(t_{final}, \text{sensor } N, \text{sensor } N) \end{bmatrix}$$

With if i is in the chain between the origin of the skeleton and the segment j $$Mat_{mvt}(t, \text{sensor } j, \text{sensor } i) = \left[-\left(\frac{\partial^{2 \, sensor \, 1} \, Rotation(t) \, Earth}{\partial t^2}\right)_{\substack{reference \, frame \, i \\ sensor}}\right]$$

And otherwise $$Mat_{mvt}(t, \text{sensor } j, \text{sensor } i) = \begin{bmatrix} 0 & 0 & 0 \\ 0 & 0 & 0 \\ 0 & 0 & 0 \end{bmatrix}$$

Once this matrix has been constructed, it merely remains to solve the following least squares problem:

$$\text{Mat\_tot}_{mvt} * PosLong = Acc_{basis\text{-}free}(t_{initial} \rightarrow t_{final})$$

With $$PosLong = \begin{bmatrix} Position_{sensor \, 1} \\ Position \, origin_{segment \, 2} \\ Position_{sensor \, 2} \\ \vdots \\ Position \, origin_{segment \, N} \\ Position_{sensor \, N} \end{bmatrix}$$

Once PosLong has been estimated, it merely remains to collect the parameters according to the provision given in the above equality.

This procedure is advantageous since it expresses the estimation in the form of a linear least squares problem, the calculation of the estimate is therefore explicit and optimal.

According to embodiments of the invention (patent application filed on the same day as the present application by the same applicants having the same inventor and having as title "PROCEDE D'IDENTIFICATION DES PARAMETRES GEOMETRIQUES D'UNE STRUCTURE ARTICULEE ET D'UN ENSEMBLE DE REPERES D'INTERET DISPOSES SUR LADITE STRUCTURE" [METHOD OF IDENTIFYING THE GEOMETRIC PARAMETERS OF AN ARTICULATED STRUCTURE AND OF AN ASSEMBLY OF REFERENCE FRAMES OF INTEREST DISPOSED ON SAID STRUCTURE], incorporated herein by reference, the measurement model is advantageously solved, even if only a reduced number of gyrometers are available to supplement the accelerometer and magnetometer measurements, by calculating pseudo-static states which can be substituted, each time that the system is in a pseudo-static state, for the values calculated by a Kalman type state observer.

These steps of the method of various embodiments of the invention can be implemented in software, certain parts of the software possibly being installed onboard the sensors, others possibly being embedded in a micro-controller, a micro-processor, or a micro-computer connected to the system of sensors. These processing capabilities can be conventional circuits, connected and configured to perform the processing operations described hereinabove.

The examples described hereinabove are given by way of illustration of embodiments of the invention. They do not in any way limit the field of the invention, which is defined by the claims which follow.

The invention claimed is:

1. A method of determining a position of an assembly of sensors in a segment reference frame associated with a segment of an articulated structure for use in capturing a motion of a body, the assembly of sensors comprising at least one accelerometer and being connected to the articulated structure, the method comprising:
- determining, based on measurements received from the accelerometer and at least one predetermined configuration of the articulated structure, an orientation of a sensor reference frame associated with the assembly of sensors with respect to the segment reference frame, wherein the determining the orientation comprises calculating a first rotation matrix for passing from the sensor reference frame to an earth reference frame and calculating a second rotation matrix for passing from the earth reference frame to the segment reference frame, wherein calculating the first rotation matrix uses at least one measurement of at least one second sensor of the assembly of sensors, the second sensor configured to provide measurements of at least one physical field which is substantially uniform over time and in space or measurements of rotation speed;
- estimating, based on the determined orientation, a predetermined motion of the sensor reference frame in the earth reference frame during at least one motion of the segment of the articulated structure;
- calculating, based on the estimated predetermined motion, the position of the assembly of sensors in the segment reference frame; and
- outputting, based on the calculated position, captured motion of the body.

2. The method of claim 1, wherein prior to calculating the first rotation matrix a third rotation matrix is calculated for passing between a motion reference frame that is in motion and the earth reference frame, the third rotation matrix being calculated on a basis of the measurements of the at least one physical field which is substantially uniform over time and in space or of the measurements of the rotational speed of the motion reference frame with respect to the earth reference frame.

3. The method of claim 1, wherein each calculation is performed for at least two configurations of the articulated structure.

4. The method of claim 1, wherein, the motion of the sensor reference frame comprises a motion with a substantially invariant axis of rotation.

5. The method as claimed in claim 1, wherein estimating the predetermined motion uses the outputs of at least one sensor chosen from the group comprising the at least one accelerometer and the second sensor.

6. The method as claimed in claim 1, wherein, in the course of estimating the predetermined motion, said at least one motion of the segment is a rotation around a substantially invariant axis.

7. The method as claimed in claim 1, wherein, in the course of at least estimating the predetermined motion and calculating the position, use is made of a predictive model of the outputs of the at least one accelerometer chosen as a function of the type of the motion of said segment and the position is calculated of said assembly of sensors on said segment as output by an algorithm minimizing errors between measured values and predicted values.

8. The method as claimed in claim 1, wherein said articulated structure comprises at least N segments, N being greater than or equal to two.

9. The method as claimed in claim 8, further comprising:
- calculating the length of at least one segment of said articulated structure.

10. The method as claimed in claim 9, wherein calculation of a segment i inserted into the articulated structure comprising j segments, j being greater than 1 and greater than i, is performed by solving the equation $$\text{Mat\_tot}_{mvt} * \text{PosLong} = \text{Acc}_{basis\text{-}free}(t_{initial} \to t_{final})$$ in which:

Mat_tot$_{mvt}$ is a matrix of dimension (i, j) whose coefficients are calculated by the formula $$Mat_{mvt}(i, \text{sensor } j, \text{sensor } i) = \left[ -\left( \frac{\partial_2^{Sensori_{Rotation(t)}Earth}}{\partial t^2} \right)_{\substack{reference\ frame \\ sensor\ j}} \right],$$

$$PosLong = \begin{bmatrix} Position_{sensor1} \\ Position\ origin_{segment\ 2} \\ Position_{sensor\ 2} \\ \vdots \\ Position\ origin_{segment\ N} \\ Position_{sensorN} \end{bmatrix}$$

PosLong is the vector

The basis-free acceleration at the instant t is calculated by the formula $$Acc_{basis\text{-}free}(t) = Meas_{Acc}(t) - G0_{referenceframe\ sensor} + Acc_{asssembly_{referenceframesensor}}.$$

11. The method as claimed in claim 9, wherein said articulated structure is a part of a human body or of a humanoid structure.

12. The method as claimed in claim 11, wherein the at least one predetermined configuration of said articulated structure is determined by execution of at least N predefined successive gestures, each gesture enabling only a rotation of all or some of the segments of said structure in a unique plane about a unique axis passing through an articulation linking two segments, the segments other than the two stated segments remaining aligned during said rotation, in such a way that rotations of segments are executed about at least N distinct axes.

13. The method as claimed in claim 12, wherein N>=3, a first segment corresponding to a shoulder, a second segment corresponding to an arm linked to the shoulder and a third segment corresponding to a forearm linked to the arm by an elbow, the execution of predefined gestures including, in order:
- a rotation of the entire body about a vertical axis, the shoulder-arm-forearm assembly being held outstretched in a horizontal plane during the rotation of the body about said axis, and;
- a rotation of the arm-forearm assembly about a horizontal axis passing through the articulation linking the shoulder to the arm, the arm-forearm assembly being held outstretched during said rotation, and;
- a rotation of the forearm about a horizontal axis passing through the elbow linking the arm to the forearm, the shoulder-arm assembly being held outstretched during said rotation.

14. The method as claimed in claim 13, wherein each rotation of segments is executed about an axis passing through an articulation.

15. A system for determining a position of an assembly of sensors in a segment reference frame associated with a segment of an articulated structure for use in capturing a motion of a body, the assembly of sensors comprising at least one accelerometer and being connected to the articulated structure, the system comprising:
- a first module for determining, based on measurements received from the accelerometer and at least one predetermined configuration of the articulated structure, an orientation of a sensor reference frame associated with the assembly of sensors with respect to the segment reference frame, wherein the determining the orientation comprises calculating a first rotation matrix for passing from the sensor reference frame to an earth reference frame and calculating a second rotation matrix for passing from the earth reference frame to the segment reference frame, wherein calculating the first rotation matrix uses at least one measurement of at least one second sensor of the assembly of sensors, the second sensor configured to provide measurements of at least one physical field which is substantially uniform over time and in space or measurements of rotation speed;
- a second module for estimating, based on the determined orientation, a predetermined motion of the sensor reference frame in the earth reference frame during at least one motion of the segment of the articulated structure;
- a third module for calculating, based on the estimated predetermined motion, the position of the assembly of sensors in the segment reference frame; and
- a fourth module for outputting, based on the calculated position, captured motion of the body.

* * * * *